United States Patent [19]

Sterrett et al.

[11] Patent Number: 5,049,068
[45] Date of Patent: Sep. 17, 1991

[54] METHOD OF USING PULSE RADIATION FOR BONDING ORTHODENTIC BRACKETS TO TEETH

[75] Inventors: Terry L. Sterrett, Long Beach; Craig A. Andreiko, Alta Loma; Ronald J. Sirney, Bloomington; Michael L. Swartz, Encino, all of Calif.

[73] Assignee: Ormco Corporation, Glendora, Calif.

[21] Appl. No.: 473,038

[22] Filed: Jan. 31, 1990

[51] Int. Cl.$^5$ ............................................. A61C 3/00
[52] U.S. Cl. ......................................................... 433/9
[58] Field of Search ........................ 433/9; 250/504 H

[56] References Cited

U.S. PATENT DOCUMENTS

| | | | |
|---|---|---|---|
| 3,745,653 | 7/1973 | Cohl | 433/9 |
| 3,782,889 | 1/1974 | Panico | 432/59 |
| 4,167,669 | 9/1979 | Panico | 250/504 |
| 4,221,994 | 9/1980 | Friedman et al. | 250/504 H |
| 4,309,617 | 1/1982 | Long | 250/504 H |
| 4,375,961 | 3/1983 | Brooks | 433/4 |
| 4,443,533 | 4/1984 | Panico | 250/492.1 |
| 4,450,139 | 5/1984 | Bussiere et al. | 250/504 R |
| 4,468,197 | 8/1984 | Provost | 433/29 |
| 4,749,352 | 6/1988 | Nicholson | 433/9 |

OTHER PUBLICATIONS

J. F. McCabe and T. E. Carrick, Output from Visible-Light Activation Units and Depth of Cure of Light Activated Composites, Mar. 3, 1989, pp. 1534,1535,1536,1537,1538,1539, vol. 68, No. II.

Primary Examiner—John J. Wilson
Attorney, Agent, or Firm—Marjama & Pincelli

[57] ABSTRACT

A method and apparatus for photopolymerizing a material using a pulsed radiation source, preferably in the visible spectrum.

14 Claims, 3 Drawing Sheets

METHOD OF USING PULSE RADIATION FOR BONDING ORTHODONTIC BRACKETS TO TEETH

The present invention is directed to a method of curing dental and orthodontic adhesive and/or resins, and more particularly, to a method wherein a photopolymerisable material is cured using a pulsed light source.

BACKGROUND OF THE INVENTION

Extensive investigation has been done in the prior art with regard to the potential use of light curing adhesive or resins for orthodontic and dental applications. Originally, these systems include usage of a photoinitiator which could be activated through exposure to an ultraviolet light. However, these type adhesive were not desirable due to the use of ultraviolet light. Further work resulted in the development of a visible light curing system. U.S. Pat. No. 4,749,352 is illustrative of a prior art method which utilize a visible light curing adhesive system for orthodontic brackets. While such systems appear to provide adequate bonding strength, they are relatively limited. Additionally, such cure systems utilize relatively long cure times to sufficiently polymerize the material. Such prior art available light sources and cure systems typically require an excitation time of approximately 20-30 seconds per tooth. The implications with respect to excessively long clinical chair time with regard to patient comfort, efficiency of the orthodontics and of course ultimate cost to the patient.

Applicants have developed an curing system wherein excitation times in the order of 3 to 4 seconds can be used in order to cure an adhesive resin through the use of a pusled wavelength radiation source.

SUMMARY OF THE INVENTION

In one aspect of the present invention, there is provided a method of photopolymerising a dental material by subjecting the material to a pulsed radiation source for a predetermined time period so as to cure the material.

In another aspect of the present invention, there is provided a method for bonding an orthodontic bracket to a tooth comprising the steps of:

applying a photopolymerisable adhesive to the bracket or tooth;

applying the bracket to the tooth in the desired position; and directing a pulsed radiation source to the bracket and tooth so as to cure the adhesive.

In yet another aspect of the present invention, there is provided an apparatus for providing a pulsed source of radiation in substantially the visible light spectrum. The apparatus includes a lamp which yields radiation in the 380-600 nanometer wavelength range. Means are provided for pulsing the lamp in the desired frequency and for the desired time period.

DETAILED DESCRIPTION OF THE INVENTION

Figure 1:
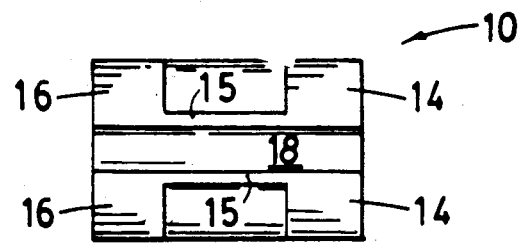
FIG. 1 is a top plan view of a transparent/translucent orthodontic bracket which may be used with the method of the present invention.
Figure 2:
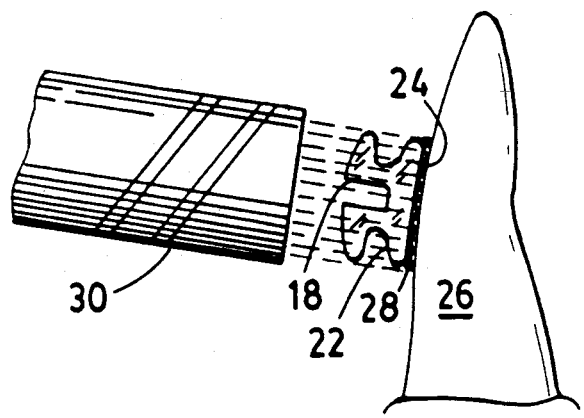
FIG. 2 is a side elevational view illustrating the orthodontic bracket of FIG. 1 being secured to a tooth using the method of the present invention.
Figure 3:
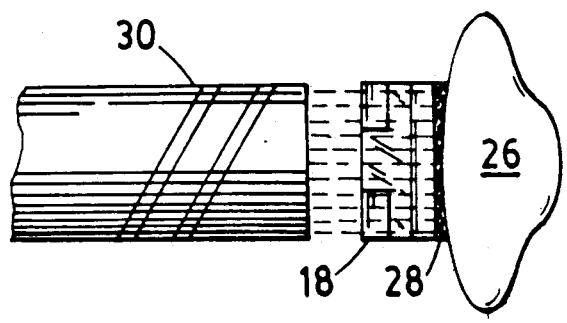
FIG. 3 is a top plan view of FIG. 2.

Referring to FIG. 1-3, there is illustrated an orthodontic bracket 10. In the preferred embodiment illustrated, the bracket 10 is made of a transparent/translucent-type material. In the particular embodiment illustrated, the bracket 10 is made out of a ceramic polycrystalline alumina material. It is, of course, understood that other transparent/translucent materials may be used. For example, but not by way of limitation, plastic, single crystalline ceramics, polycrystalline zirconium, glass, and other ceramics. Additionally other non-transparent/translucent-type materials may be used for bracket 10 that are presently available or that may be developed in the future.

In the embodiment illustrated, the bracket 10 is provided with a pair of tie wings 14, 16 which are connected by connecting portions 15 which combine together to form an orthodontic archwire slot 18 for receiving an orthodontic archwire (not shown) as is customarily done in the prior art. It is to be understood that various other configurations may be used, for example, but not limited to, single wing and twin wing-type constructions as are well known in the prior art. The bracket 10 includes a base 22 having a tooth contact surface 24 which is placed against the surface of the tooth 26. Placed between the contact surface 24 and tooth 26 is an adhesive layer 28 which is photopolymerisable by exposure to a source of radiation, preferably visible light. The bracket 10 is placed on a tooth 26 as is customarily done in the prior art by applying an adhesive to the contact surface 24 of the bracket 10 and/or tooth, and the bracket 10 being directly applied to the tooth. Thereafter, a radiation source is used to photopolymerize the adhesive layer 28. Since the bracket 10 in the preferred embodiment is made of a transparent/translucent material, the radiation source 30 is placed directly above the bracket 10 as illustrated in FIG. 2 and turned on for an appropriate period of time so as to sufficiently cure the adhesive layer 28. As previously noted, the adhesive layer 38 is of a photoinitiator type, i.e., being capable of being polymerized when exposed to a radiation source. In the embodiment illustrated, adhesive layer 28 is capable of being polymerized by the use of a substantially visible light source, i.e., a light source having primary emission in the 380-600 nanometer wavelength region. For the purpose of this invention, a substantially visible light source may have up to about 20% ultraviolet light. The light source 30 is preferably pulsed at a frequency in the range of $0.01s^{-1}$ (100 times per second) to $0.50s^{-1}$ (two times per second). In the particular embodiment illustrated, the radiation source comprised a cerium doped lamp which yields radiation from about 380-600 nanometer wavelength. A suitable cerium doped lamp may be purchased from Zeon Corporation using a tube purchased from Heraus QuarzschMeize Gmbh model M 382. The lamp reaches a peak power of about $1 \times 10^6$ watts for an exposure time of about $1 \times 10^{-3}$ seconds. The lamp is pulsed ten times per second. The pulsing of the lamp is accomplished in a manner as is customarily done in the prior art, for example, as done by the Xeon Corporation. A suitable adhesive is sold under TRANSBOND trademark by Unitek. Preferably, the adhesive is of the type wherein post-light exposure excitation continues to take place such as occurs with the TRANSBOND light cured adhesive.

In order to more fully understand the method of bonding orthodontic brackets to the teeth according to the present invention, a detailed explanation will now be discussed. The surface of the teeth in the area to which brackets are to be applied are prepared as in customarily done in the prior art. In the present invention, this is accomplished by first polishing the teeth with a prophylaxis paste such as pumice. The teeth are then rinsed with water and then dried with warm air. The teeth are then prepared for bonding by etching the surface for about 90 seconds at room temperature with 37% by weight phosphoric acid. It is, of course, understood that various other acids may be used, and other appropriate time periods may be used as required. The teeth are then rinsed with distilled water for approximately 30 seconds. Next, the teeth are dried with warm air. Next in the desired other, a bracket is applied to each tooth. A photopolymerisable adhesive is then applied to the surface of a tooth or bracket. In the preferred practice, the adhesive would be placed directly to the contact surface 24 of the bracket 10. The bracket 10 would then be applied to the tooth in the desired area and pressed against the tooth so as to cause any excess adhesive to be expelled from behind the base 22. Any excess adhesive is then cleaned and removed. Thereafter, a visible pulsed light source 30 is directed to the bracket 10 and tooth so as to cure the bonding adhesive. In the particular embodiment illustrated in FIGS. 1-3, the light source is held about 1-2 mm directly above the bracket 10 for a time period of approximately 3-4 seconds.

In applications were dental restoratives, veneers, etc. are to be cured, the same technique is used for the placement of the light source and excitation time. The preparative methods used for the procedure will vary in accordance to dental material used, tooth structure and dental procedure. It is, of course to be understood that variation in procedures may occur in relationship to dental procedure to be performed and material to used.

Figure 4:
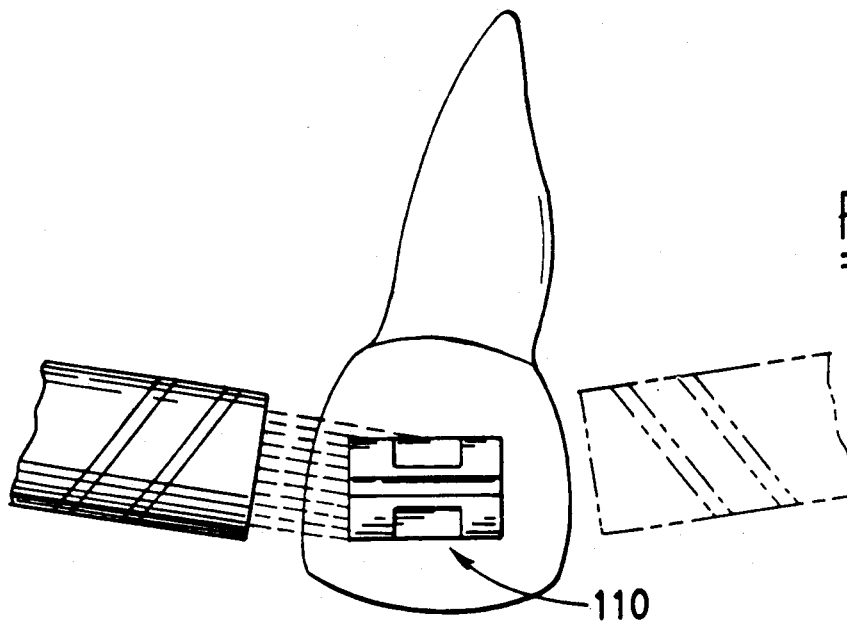
FIG. 4 is a front elevational view of a bracket having an opaque color placed against the tooth and the application of a radiation source in accordance with the present invention.
Figure 5:
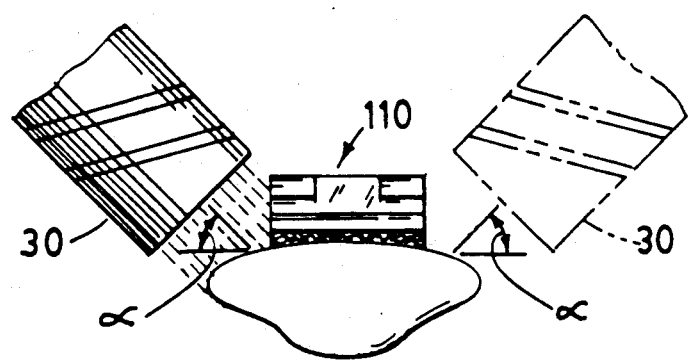
FIG. 5 is a top plan view of the FIG. 4.

Referring to FIGS. 4-5, there is illustrated an orthodontic bracket 110 being made of metal (e.g. steel) in a configuration that is customarily found in the prior art. Bracket 110 is similar to bracket 10, like numerals indicating like parts. In positioning the light source 30 with respect to the bracket 110, light source 30 is first placed at an angle of about 45° in the mesial distal orientation as illustrated by solid lines in FIGS. 4-5. The light source 30 is then excited for the appropriate period of time, i.e. approximately 3-4 seconds, and moved to the position illustrated by dash lines in FIGS. 4-5 on the other mesial distal side of the bracket 10. The light source 30 is again excited for about 3-4 second time period. Two applications are preferred due to the opaque nature of the metal bracket 110.

Applicants have found that an orthodontic bracket bonded in accordance with the present invention can be bonded in a substantially less period of time than a conventional continuous wavelength light soruce techniques. Brackets that were cured using the pulsed light source according to the present invention, have equal or greater strength properties than those cured by using continuous wavelength light source of the prior art which require light exposures in the order of approximately 30 seconds. Table A illustrates a comparison of brackets bonded in accordance with the present invention as compared to brackets bonded using a continuous wavelength light source. Both ceramic and metal brackets were tested with two different photoinitiator adhesives. Results of such comparisons are illustrated in Table A.

TABLE A

| CURE DESCRIPTION | SHEAR BOND CERAMIC (MPa) | STRENGTH METAL (MPa) | DIAMETRAL TENSILE (MPa) |
| --- | --- | --- | --- |
| Control Continuous Light Adhesive A 30 Sec | 15.79 ± 2.75 | 5.69 ± 1.67 | 41.99 ± 7.07 |
| Pulsed Light 3 Sec Cure Adhesive A | 14.22 ± 0 | 7.06 ± 1.18 | 42.22 ± 2.5 |
| Pulsed Light 4 Sec Cure Adhesive A | 15.30 ± 0.47 | 7.06 ± 4.22 | 46.61 ± 4.36 |
| Control Continuous Light Adhesive B 30 Sec | 7.46 ± 1.28 | 3.04 ± 0.98 | 24.44 ± 4.23 |
| Pulsed Light 3 Sec Cure Adhesive B | 7.46 ± 2.26 | 2.35 ± 0.98 | 19.24 ± 4.14 |
| Pulsed Light 4 Sec Cure Adhesive B | 7.65 ± 4.81 | 2.55 ± 1.86 | 18.84 ± 4.23 |

Figure 8:
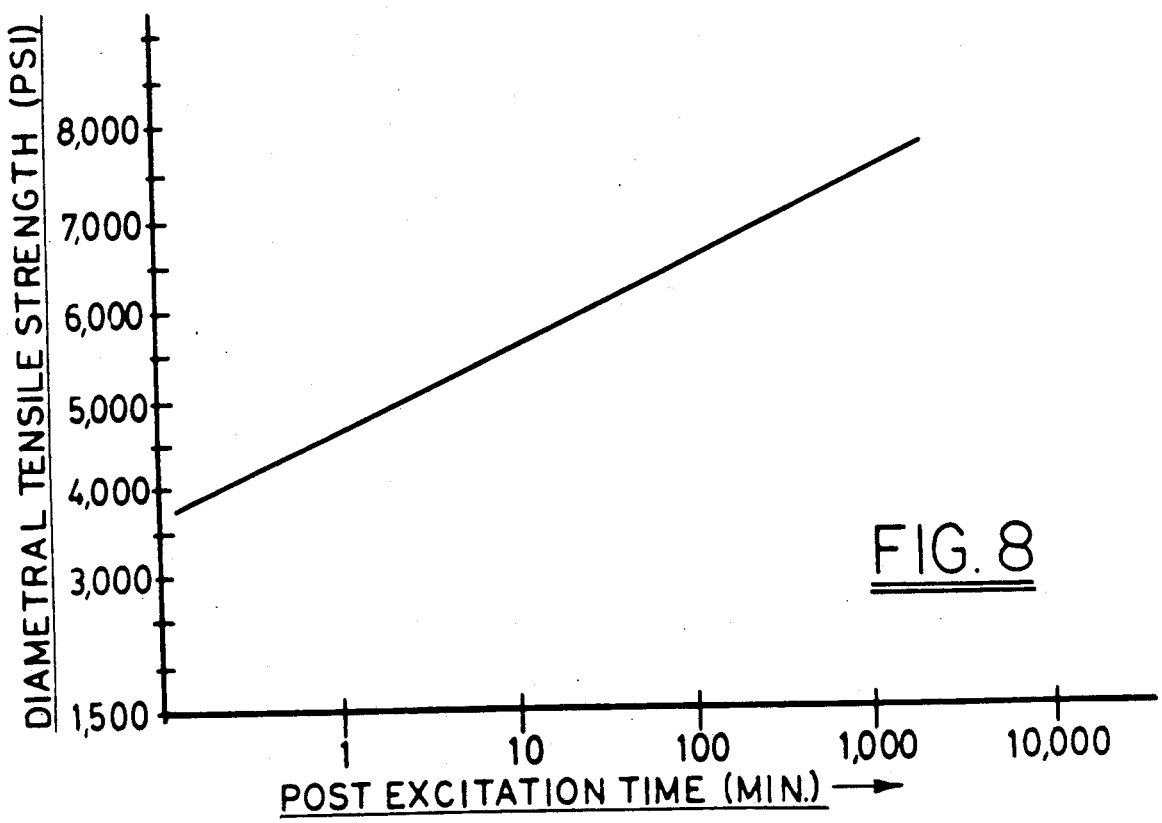
FIG. 8 is a graph of tensile strength versus post-excitation time for a light cured adhesive used to bond the bracket to the tooth.

The control was cured in an identical manner with that of the pulse light source except the control was exposed for a period of 30 seconds. In the case of the metal brackets, exposure occurs for 30 seconds per side per bracket. The control light source was a continuous wavelength light source which emits light in the visible range which is commercially available by Kerr. Manufacturing Company sold under the COMMAND trademark. The pulsed radiation source comprised a commercially available lamp from Xeon Corporation, Model RC250A. The adhesive identified as Adhesive A is an adhesive sold by Unitek under the TRANSBOND trademark and the second adhesive B is an adhesive sold by Reliance under the LIGHT BOND trademark. Both adhesives capable of being cured when exposed to visible light, light outside the visible spectrum having no substantially affect on cure. Cure times of about 3 and 4 seconds were obtained for the pulsed light source and cure times of about 30 seconds was obtained for the continuous light source. The TRANSBOND adhesive provided better results in that post-excitation curing occurred for a period up to about 24 hours after excitation. That is, the adhesive continued to cure even after exposure to light as illustrated in FIG. 8 which plots time versus diametral tensile strength for the TRANSBOND adhesive. By pulsing the light, a greater amount of energy can be transmitted to the adhesive without adversely affecting the patient. For example, a typical continuous 500 watt light source produces about 500 Joules for a 1 second exposure time period. Using pulsed radiation, a light source which produces 500,000 watts for a $1 \times 10^{-3}$ second time period can deliver 500 Joules in 1 millisecond. By simply pulsing the light source 10 times per second, ten times the amount of energy can be delivered. These short bursts of energy contribute to minimizing the amount of heat developed.

Figure 6:
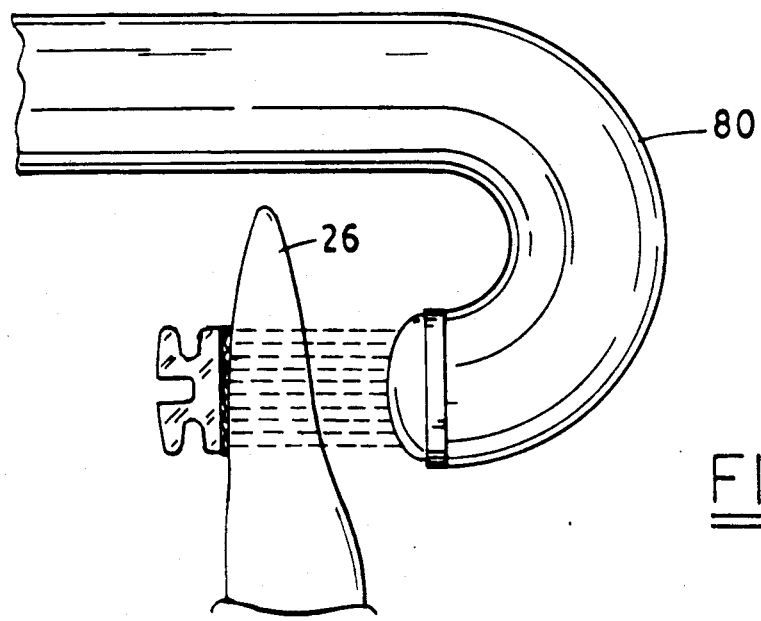
FIG. 6 is a side elevational view of an orthodontic bracket being secured to a tooth using a modified method in accordance with the present invention.
Figure 7:
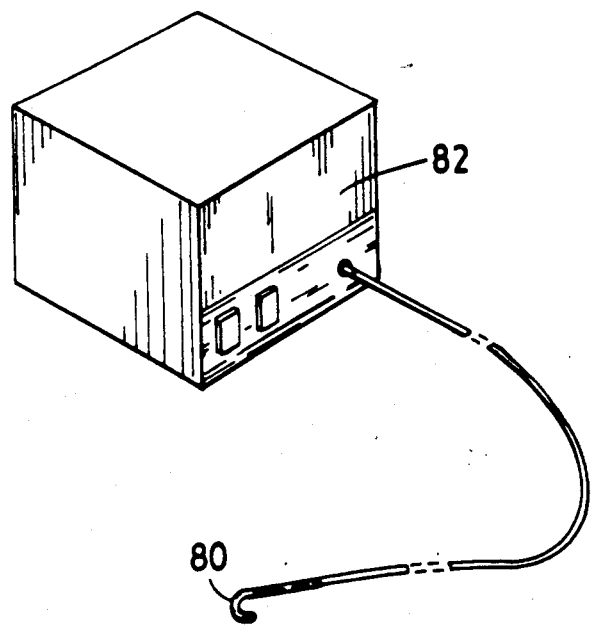
FIG. 7 is a perspective view of an apparatus used to practice the method of the present invention.

In addition to providing more energy faster, the high peak energy pulses have the advantage of being able to penetrate thick and certain opaque material. Thus, making it possible to cure the adhesive by delivering the curing radiation through the tooth which is translucent. Referring to FIG. 6, there is illustrated an orthodontic bracket 10 placed on the labial side of the tooth. A radiation energy source is directed to the lingual side of the tooth so as to cure the adhesive layer between the tooth and bracket. A liquid light tube 80 is used to direct the light to the liquid side of the tube. The liquid light tube is configured so as to properly direct the light to the labial side of the tooth. In the particular embodiment illustrated in FIGS. 6 and 7, light tube 80 has a substantially U-shaped configuration and is connected to a source of pulsed light 82. The light source 82 has disposed therein an appropriate lamp as previously discussed which is activated by conventional means. Liquid light tubes are commercially available and may be purchased from Xeon Corporation.

In the particular embodiment illustrated in FIG. 6, the bracket 110 is opaque, and more particularly, is made of metal. Thus an opaque bracket can be effectively adhered to the tooth by the single application of a radiation source. A further advantage of curing the adhesive through the tooth is that a more uniform exposure of the adhesive can be obtained resulting in a uniform and consistent cure as opposed to systems wherein only the edges of the adhesive are exposed to the radiation source.

While the present invention has been described with respect to curing an adhesive for bonding orthodontic brackets, the method of the present invention can be utilized for the curing of other orthodontic or dental materials, for example, but not limited to, resins used to fill teeth, decay prevention applications, cosmetic bonding, cosmetic dental applications (veneers), restoration of teeth, and dental attachment of devices to tooth structures (bridges).

It is, of course, understood that various changes and modifications may be made without departing from the scoper of the present invention. The present invention being defined by the following claims.

We claim:

1. A method for bonding orthodontic brackets to teeth comprising the steps of:
   a) applying a photopolymerisable adhesive to the base of the bracket or a tooth;
   b) applying the bracket to said tooth in the desired position; and
   c) directing a pulsed radiation source to said bracket and tooth so as to cure said photopolymerisable adhesive.

2. The method according to claim 1 wherein said pulsed radiation source has a primary emission in the visible spectrum wavelength region.

3. The method according to claim 1 wherein said pulsed radiation source has an emission in the 380 to 600 nanometer wavelength region.

4. The method according to claim 1 wherein said pulsed radiation source reaches a peak power in the range of about $1 \times 10^6$ watts.

5. The method according to claim 1 wherein the pulsed radiation source is pulsed at a frequency in the range of $0.01 s^{-1}$ to $0.50 s^1$.

6. The method according to claim 1 wherein the pulsed radiation source is pulsed 10 times per second.

7. The method according to claim 1 wherein said pulsed radiation source is directed at said bracket and tooth for a time period in the range of about 3-5 seconds.

8. The method according to claim 1 wherein said bonding adhesive includes a means for continuing to cure the adhesive during post-radiation excitation.

9. The method according to claim 1 wherein a plurality of orthodontic brackets are simultaneously subjected to said pulsed radiation source so as to cure said photopolymerisable adhesive.

10. The method according to claim 1 wherein said pulsed radiation source is directed through the bracket.

11. The method according to claim 1 wherein said placed radiation source is directed toward said bracket through said tooth.

12. The method according to claim 1 wherein pulsed radiation source is directed to said bracket at two angled positions.

13. The method of bonding orthodontic brackets to teeth comprising the steps of:
   a) cleaning and preparing the surface of the teeth in the area to which the bracket is to be applied;
   b) rinsing the teeth and then drying said teeth;
   c) etching the surface of the teeth for a predetermined time;
   d) rinsing said teeth with water;
   e) drying said teeth;
   f) applying a photopolymerisable adhesive to the surface of the tooth or bracket;
   g) applying the bracket to the tooth in the desired area; and
   h) directing a visible pulsed radiation source toward said bracket and tooth so as to cure said bonding adhesive.

14. The method of bonding orthodontic brackets to teeth comprising the steps of:
   a) cleaning and preparing the surface of the teeth in the area to which the bracket is to be applied;
   b) applying a photopolymerisable adhesive to the surface of the tooth or bracket;
   c) applying the bracket to the tooth in the desired area; and
   d) directing in visible pulsed radiation source toward said bracket and tooth so as to cure said bonding adhesive.

* * * * *